United States Patent
Guglielmi et al.

[11] Patent Number: 5,976,131
[45] Date of Patent: Nov. 2, 1999

[54] DETACHABLE ENDOVASCULAR OCCLUSION DEVICE ACTIVATED BY ALTERNATING ELECTRIC CURRENT

[75] Inventors: Guido Guglielmi, Santa Monica; Cheng Ji, Los Angeles, both of Calif.

[73] Assignee: The Regents of the University at California, Oakland, Calif.

[21] Appl. No.: 08/666,804

[22] Filed: Jun. 18, 1996

Related U.S. Application Data

[63] Continuation-in-part of application No. 08/323,662, Oct. 17, 1994, Pat. No. 5,569,245, which is a continuation-in-part of application No. 08/311,508, Sep. 23, 1994, Pat. No. 5,540,680, which is a continuation of application No. 07/840,211, Feb. 24, 1992, Pat. No. 5,354,295, which is a continuation-in-part of application No. 07/492,717, Mar. 13, 1990, Pat. No. 5,122,136.

[51] Int. Cl.⁶ .................................................. A61B 17/39
[52] U.S. Cl. ................................ 606/49; 606/32; 606/40
[58] Field of Search ................................ 606/32, 41, 40, 606/49

[56] References Cited

U.S. PATENT DOCUMENTS

| | | | |
|---|---|---|---|
| 5,122,136 | 6/1992 | Guglielmi et al. | 606/41 |
| 5,354,295 | 10/1994 | Guglielmi et al. | 606/32 |
| 5,743,905 | 4/1998 | Eder et al. | 606/32 |

*Primary Examiner*—Lee Cohen
*Attorney, Agent, or Firm*—Daniel L. Dawes

[57] ABSTRACT

An apparatus is provided for electrocoagulating blood and tissue at an occlusion site by means of application of an alternating signal or current through a detachable partially insulated coil on the end of a microcatheter. A Guglielmi Detachable Coil (GDC) is preferably used in the combination with damped radio frequency energy to cause local heating at the location of the coil but without local ohmically heated tissue damage or hot spots. Damping of the radio frequency energy facilitates the avoidance of hot spots. Once carbonization of blood at the detachment zone of the GDC coil occurs, the impedance of the entire system increases. The impedance increase is detected to automatically turn off the alternating current and then to apply a direct current to electrolytically detach the GDC coil from the microcatheter.

26 Claims, 2 Drawing Sheets

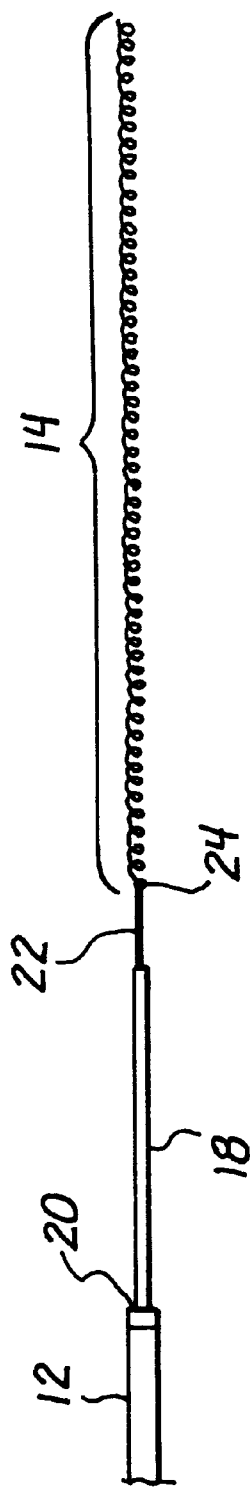
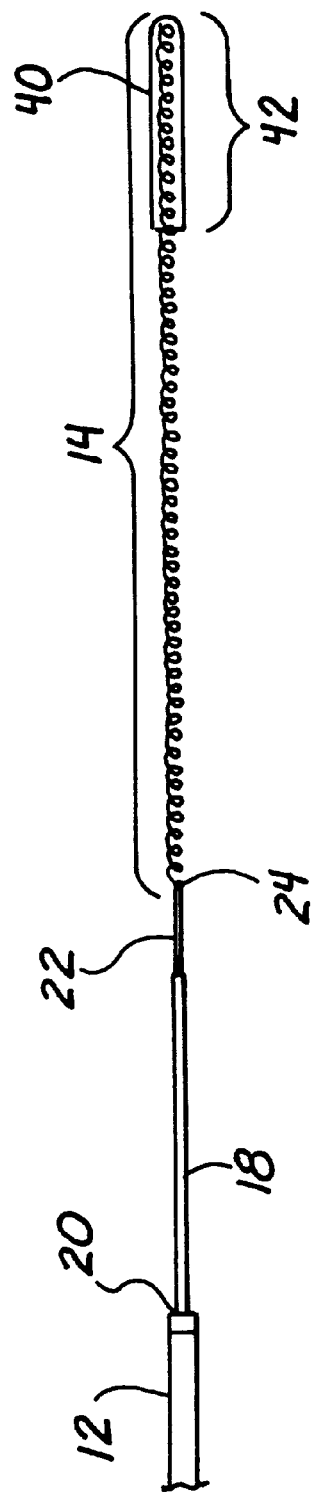

DETACHABLE ENDOVASCULAR OCCLUSION DEVICE ACTIVATED BY ALTERNATING ELECTRIC CURRENT

This application is a continuation-in-part of U.S. patent application Ser. No. 08/323,662, entitled DETACHABLE ENDOVASCULAR OCCLUSION DEVICE ACTIVATED BY ALTERNATING ELECTRIC CURRENT, filed Oct. 17,1994 which issued as U.S. Pat. No. 5,569,245, which was a continuation-in-part of application Ser. No. 08/311,508 filed Sep. 23, 1994, now U.S. Pat. No. 5,540,680, which in turn was a continuation of application of Ser. No. 07/840, 211 filed Feb. 24, 1992 and issued as U.S. Pat. No. 5,354, 295, which in turn was a continuation in part of 07/492,717 filed Mar. 13, 1990 which issued as U.S. Pat. No. 5,122,136.

BACKGROUND OF THE INVENTION

1. Field of the Invention

The invention relates to the field of electrocoagulation, and in particular to the use of alternating currents to form endovascular occlusions.

2. Description of the Prior Art

Occlusion of vascular structures by endovascular catheters is currently realized though the use of detachable balloons, injectable glue, detachable or pushable coils, and injectable particles. Detachable balloons are of such a nature that they can only be practically used in large vessels. The use of injectable glue is limited by the difficulty of controllable delivery to the desired occlusion site. Detachable and pushable coils are effective, but in some cases are not sufficiently thrombogenic. The use of injectable particles suffers from their relative invisibility in fluoroscopy and the difficulty in controlling their ultimate disposition at the desired occlusion site. In many prior art technologies the coagulation wire must be ripped out of the clot, usually causing considerable disruption or even reopening the occlusion.

The use of both alternating and direct current for creating electrocoagulation is well known. See, Gold et al., "Transarterial Electrocoagulation Therapy of a Pseudoaneurysm in the Head of the Pancreas, " American Journal of Roentgenology, Volume 125, No. 2, at 422 (1975); Thompson et al., "Vessel Occlusion with Transcatheter Electrocoagulation: Initial Clinical Experience, " Diagnostic Radiology at 335 (November 1979); Thompson et al., "Transcatheter Electrocoagulation: A Therapeutic Angiographic Technique for Vessel Occlusion, " Investigative Radiology at 146 (March-April 1977); Phillips, "Transcatheter Electrocoagulation of Blood Vessels, " Investigative Radiology at 295 (September-October 1973); and Phillips et al., "Experimental Closure of Ateriovenous Fistula by Transcatheter Electrocoagulation," Diagnostic Radiology 115:319 (May 1975). However, each of these experimental investigations were generally performed in larger vessels and did not establish controllability, nor efficacy for use in smaller vessels.

Therefore, what is needed is a clinical occlusive device which is visible, biocompatible, controllable in that it can be detached at will at a desired site even distal to the delivery microcatheter, which is directable, efficacious in coagulating blood and vessel and usable in small vessels without the risk of causing disruption or reopening the occlusion at the end of the treatment.

BRIEF SUMMARY OF THE INVENTION

The invention is an apparatus for selectively providing endovascular occlusion in a patient comprising a delivery wire guidable to or near an endovascular occlusion site. A detachable coil is temporarily and selectively coupled to the delivery wire. An alternating current generator is selectively coupled to the detachable coil for delivering damped RF power signals to the occlusion site. As a result, a controllable occlusive apparatus efficacious and usable in small vessels is provided.

The apparatus further comprises a direct current generator selectively coupled to the detachable coil, and a switch for selectively coupling the alternating current generator and direct current generator to the detachable coil.

The coil is at least partially insulated. The coil has a distal tip and is partially insulated at the distal tip to reduce nonuniform ohmic heating arising from direct contact of the distal tip with tissue at the occlusion site. The coil is selectively insulated to reduce nonuniform ohmic heating arising from direct contact of between the coil and tissue at the occlusion site.

The alternating current and the direct current generators are variably controllable, in addition to which the controllable alternating current generator is frequency controllable.

The apparatus further comprises a sensing circuit for determining when a predetermined state of electrocoagulation is achieved at or near the detachable coil. The sensing circuit senses impedance of the detachable coil within the patient.

The apparatus further comprises a control circuit for selectively initiating detachment of the coil when the sensing circuit determines the predetermined state of electrocoagulation has been achieved.

The alternating current generator serves to ohmicly heat the detachable coil and surrounding blood and tissues,. but local overheating is at least reduced by disposition of an insulator on at least a portion of the coil where the coil directly contacts the tissues. In addition in one embodiment, the alternating current generator serves to dielectricly heat the detachable coil and surrounding blood at a radio frequency.

The invention is also a method of forming a vascular occlusion comprising the steps of providing a conductive delivery wire, disposing a conductive coil coupled to the delivery wire at or near a selected occlusion site, and applying an alternating current to the coil to coagulate the occlusion site without substantial local ohmic heating between contact points between the coil and the occlusion site. A determination is made whether a predetermined amount of electrocoagulation has occurred at the occlusion site. The alternating current through the coil is terminated when the step of determining establishes that the predetermined electrocoagulation has occurred. The coil is detached from the delivery wire to leave the coil at the occlusion site. As a result, an occlusion is efficaciously provided in a small vessel.

In the illustrated embodiment the coil is at least partially insulated to define insulated and noninsulated portions of the coil so that application of the alternating current to the coil is through only the noninsulated portions of the coil. the insulated portions selected to include at least one of the contact points.

Similarly, the invention is defined as a method of forming a vascular occlusion comprising the steps of providing a conductive delivery wire and disposing a conductive coil coupled to the delivery wire at or near a selected occlusion site. A damped alternating current is applied to the coil to coagulate the occlusion site. A determination is made whether a predetermined amount of electrocoagulation has occurred at the occlusion site. The alternating current through the coil is terminated when the step of determining establishes that the predetermined electrocoagulation has occurred. The coil is detached from the delivery wire to leave the coil at the occlusion site. As a result, an occlusion is efficaciously provided in a small vessel. The damped alternating current is applied to the coil to coagulate the occlusion site in a manner to reduce ohmic heating damage to or hot spots at the occlusion site.

The invention is still further defined as an occluding device comprising an elongated body member having a proximal end, a distal end, and a body length between the proximal and distal ends. A detachable joint is attached to the proximal end of the body member. The joint is capable of conducting an electrical current to the body member. The body member is comprised of at least a proximal conductive region comprising a conductive material and a distal insulated region having a length between about 5 and 25% of the body length.

The body member may take the form of a helically wound coil. The insulated distal end or the distal insulated region may be comprised of an insulator, or the insulated region may be comprised of a core of a conductive material and an insulated covering.

The invention may be better visualized by now turning to the following drawings wherein like elements are referenced by like numerals.

BRIEF DESCRIPTION OF THE DRAWINGS

FIG. 2 is an enlarged view of one embodiment of the catheter for use in connection with the apparatus of FIG. 1.

FIG. 3 is a second embodiment of the catheter tip used in connection with the apparatus of FIG. 1.

The invention and its various embodiments may now be better understood by turning to the following detailed description.

DETAILED DESCRIPTION OF THE PREFERRED EMBODIMENTS

An apparatus is provided for electrocoagulating blood and tissue at an occlusion site by means of application of an alternating signal or current through a detachable partially insulated coil on the end of a microcatheter. A Guglielmi Detachable Coil (GDC) is preferably used in the combination with damped radio frequency energy to cause local heating at the location of the coil but without local ohmicly heated tissue damage or hot spots. Damping of the radio frequency energy facilitates the avoidance of hot spots. Once carbonization of blood at the detachment zone of the GDC coil occurs, the impedance of the entire system increases. The impedance increase is detected to automatically turn off the alternating current and then to apply a direct current to electrolytically detach the GDC coil from the microcatheter.

The apparatus of the invention uses a detachable microcatheter coil system and a source of alternating and direct electric current. The electrolytically detachable coil system is commercialized by Target Therapeutics of California as the Guglielmi Detachable Coil System (hereinafter defined as the GDC coil or system) and includes a source of direct current coupled to a microcatheter-guided wire with an electrolytically detachable distal coil. Any one of the embodiments described in U.S. Pat. Nos. 5,122,136; 5,226,911; and/or 5,354,295 may be used in the present apparatus. All of the U.S. Pat. Nos. 5,122,136; 5,226,911; and 5,354,295 are incorporated herein by reference as if set forth in their entirety. Mechanical means for detachment of the coil from the catheter is disclosed in U.S. Pat. Nos. 5,234,437 and 5,261,916 also incorporated herein by reference. The invention includes the use of not only GDC coils, but any type of detachable coil including those detachable by mechanical, thermal, optical, electrical, electromagnetic means or combinations of these various means.

Figure 1:
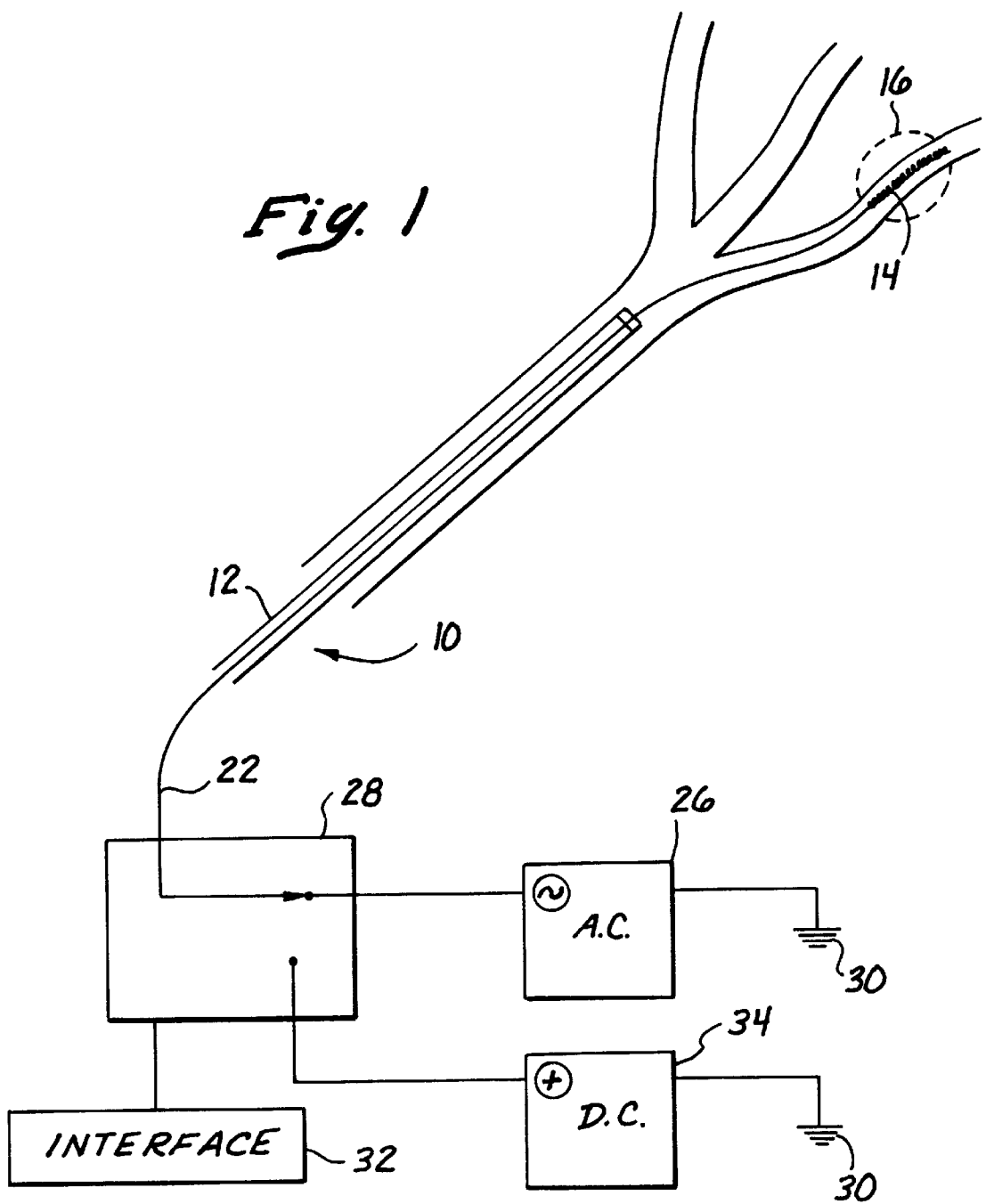
FIG. 1 is an idealized diagram of the apparatus of the invention.

FIG. 1 is a highly diagrammatic depiction of the apparatus as applied to form an endovascular occlusion. The GDC system, generally denoted by reference numeral 10, includes a guidable microcatheter 12, which in the illustrated embodiment is a tracker endovascular catheter as manufactured by Target Therapeutics, Inc. of Fremont, Calif. A GDC coil 14 is positioned at or proximate to a selected occlusion site 16, which is typically in a small vessel. GDC coil 14 is generally fabricated from platinum and may assume any physical shape, form or composition described in the foregoing incorporated patent references or known in the art. For example, GDC coil 14 may be straight, curved, circular, spiral, biased to form a preferred shaped, or completely limp and pliable, and may incorporate fibers or other equivalent micro-obstructive structures. The apparatus of FIG. 1 is particularly useful for arterial feeder occlusion of arteriovenous malformations, arteriovenous fistulae and vascular tumors.

For example, in the embodiment of FIG. 2, microcatheter 12 is shown as carrying an insulated guidewire 18 extending from catheter tip 20. At a predetermined position, insulated guidewire 18 is stripped of its insulation to provide a bare wire 22 connected at junction 24 to GDC coil 14.

GDC coil 14 is positioned at or near site 16 and an alternating signal generator 26 is connected through switching circuit 28 to a proximal end of delivery wire 22. As is conventional in the art, the alternating current is applied at a frequency, voltage, current repetition time, wave shape and other signal characteristic as may be desired to induce electrocoagulation of blood and body tissue in contact with and in the immediate vicinity of the noninsulated exposed portion of GDC coil 14 and wire 22 at the distal end of microcatheter 12. No electrocoagulation occurs in contact with or in the immediate vicinity of the insulated portion 18 of delivery wire 22.

A ground electrode 30 is provided to the patient through means of a conductive dermal adhesive pad, symbolically shown in FIG. 1 schematically as an electrical ground 30. The alternating signal or current applied through GDC coil 14 induces heating in the proximity of the noninsulated platinum portion of the GDC coil and/or the tissue such as the arterial or vessel wall and blood surrounding GDC coil 14. The insulated portion of the delivery wire should extend to almost 0.5 mm of the solder joint 24 holding coil 14, so that when alternating current or RF is applied, a clot will form substantially only around the detachable coil 14 and not the delivery wire. The frequency which is contemplated as being used and the present apparatus includes very low frequencies just above direct current to radio frequencies spanning the spectrum from less than 1 Hertz to many Gigahertz. For example, a frequency can be chosen to match a radio frequency absorption peak for any of the constituents at occlusion site 16, such as water. The proteins of the vascular structure or the blood are denatured by the heat and the shrinkage of the vascular wall and/or clotting of blood will occur. For example, it is well known that collagen fibers in the vascular wall are shrinkable at temperatures above 60 degrees centigrade.

An alternative embodiment is illustrated in FIG. 3 which is identical to that of FIG. 2 except that coil 14 is all or partially insulated. In the illustration of FIG. 3 the distal tip portion 42 is insulated by a plastic encapsulation 40. Alternatively, tip portion 42 may be provided with a thin film insulation conforming to the helical shape of coil 14 to leave tip portion 42 in substantially the same condition with respect to flexibility or stiffness as the remaining noninsulated portion of coil 14. The purpose of insulation 40 in whatever form it takes is to provide electrical insulation between coil 14 and the body tissues. In some cases depending on frequency and power levels, the possibility for tissue damage may occur if significant ohmic heating is established in the tissue through current delivered to the tissue through a contacting portion of coil 14. Typically, the distal tip portion 42 of coil 14 may physically contact the surrounding tissue making a path of least resistance of the current into the tissue and therefore concentrating current flow at that point. The ohmic heating then in the tissue can in some cases become concentrated at this point with the potential for tissue damage or at least nonuniform coagulation. Therefore, it is within the scope of contemplation of the invention that more than just the tip portion 42 of coil 14 may be insulated or partially insulated. For example, tip portion 42 may have a coating of very high resistivity while the remaining portion of coil 14 may have a coating of substantially lower resistivity. Striated insulation may also be employed to selectively control the size of the direct electrical contact area of coil 14 at different longitudinal points on coil 14 with the surrounding tissue, fluid or blood.

The power provided by alternating signal generator 26 is variable by the operator through an interface unit 32 coupled thereto either directly or through switching circuit 28. Variability of the power, the voltage, current and repetition rate through interface 32 of the output of alternating current generator 26 is used to achieve vascular occlusion without damaging the vessel wall, and to minimize or even substantially avoid unintended or unwanted heating of the surrounding tissues. Alternating signal generator 26 is a variable alternating current generator with a voltage in the range of 0 to 3000 volts. The generator is battery operated with rechargeable batteries or operated off line voltage. The waveform shape is selectable through interface 32 and typically may be sine wave, square wave, triangular wave or customized shapes with a variable frequency or pulse rate.

Figure 4:
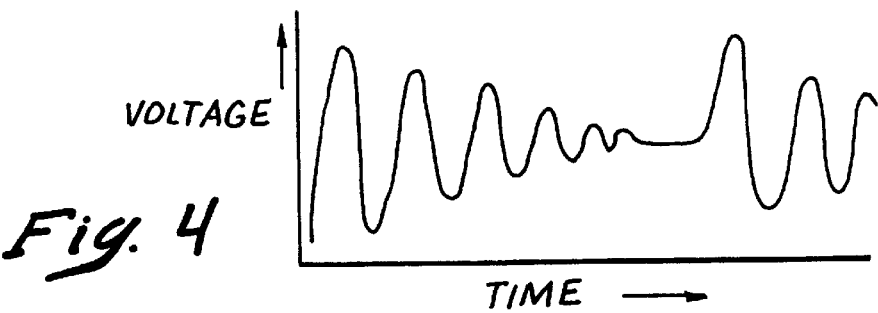
FIG. 4 is a waveform diagram of damped RF excitation applied to the coil of the invention.

The RF waveform applied to coil 14 may be modulated in any manner now known or later devised to selectively control the power or rate of change at which power is delivered by coil 14 into the tissue. For example, the RF waveform may be controllably damped as shown in FIG. 4 so that the energy input by each pulse into the tissue is delivered at an instantaneous rate which allows for heat dissipation to avoid or lessen tissue damage to ohmic heating. While thermal dissipation time constants in tissue are generally much slower than any of the time parameters of the RF envelope, and while it is not completely understood why damped RF waveforms are less likely to damage tissue in the context of an endovascular heating coil, the fact has been observed.

The waveform of the alternating current signal is continuously monitored through interface 32 and vessel occlusion is instantly detected by changes in the shape of the waveform due to carbonization of the blood on the detachment zone in the proximity of junction 24 on GDC coil 14. This waveform change due to blood carbonization is determined by a change in the impedance of the system shown in FIG. 1. Therefore, interface 32 is contemplated as included an impedance detector which will automatically sound an audible signal to the operator or trigger an automatic turn off of the alternating current generator 26. Once sufficient coagulation has been determined to have occurred, GDC coil 14 is detached as described in the incorporated patent references by means of a direct current generated by direct current generator 34 and coupled through switching circuit 28 to delivery wire 22. Switching circuit 28 may be manually activated by the operator, or automatically programmed to switch over to deliver the proper direct current separating current at the completion of alternating current electrocoagulation.

GDC coils 14 are particularly effective in the apparatus of FIG. 1. In contrast to other types of endovascular coils, GDC coils 14 are detachable in place and distal from delivery catheter 12 after vessel occlusion has been achieved. Coils of various sizes, ranging from 0.005 to 0.2 inch in diameter, various shapes and configurations and softness utilizing metallic or conductive wire diameters in the range of 0.001 to 0.004 or more inch can be used as desired for coil 14. Conductive wires with different electrical resistances may be utilized. Platinum wire is preferred, but any conductor, including nonmetallic conductors can be substituted.

Although the embodiment of FIG. 1 has been shown with alternating current generator 26 and direct current generator 34 as separate units, it is expressly contemplated that both units, as well as interface 32 together with an impedance detection circuit as described above, will be integrally incorporated within a single circuit. The impedance detector subcircuit thus automatically will turn off the alternating current signal and activate the direct current signal to detach the GDC coil 14. In this embodiment, the operator, after setting the initial parameters, need only then to turn on a single activate switch to cycle through a complete procedure. Acoustic or audio visual feedback can be provided to display both alternating current vessel occlusion and detachment of GDC coil 14. For example, both the direct current and alternating current components of the signal may be digitally generated through a personal computer software controlled interface. Power levels are low, being typically in the range of 0.1 to 20 watts so that the use of broadband generators is feasible. Alternatively, interface 32 may be used to selectively couple two or more separate generators to catheter 12 to completely cover the desire frequency bands discussed above.

While a conventional guidewire 22 is adequate for transmission of direct current to MHz signals, it is conceivable that power losses at higher frequencies in the GHz bands may become unacceptable. Therefore, guidewire 22 in these cases may be alternatively fabricated in the form of a flexible micro-coaxial cable, microwave transmission stripline or other transmission means now known or later devised as may be appropriate for carrying the power levels and frequencies disclosed.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims.

The words used in this specification to describe the invention and its various embodiments are to be understood not only in the sense of their commonly defined meanings, but to include by special definition structure, material or acts beyond the scope of the commonly defined meanings. The definitions of the words or elements of the following claims are, therefore, defined in this specification to include not only the combination of elements which are literally set forth, but all equivalent structure, material or acts for performing substantially the same function in substantially the same way to obtain substantially the same result.

In addition to the equivalents of the claimed elements, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. An apparatus for selectively providing endovascular occlusion in a patient comprising:
   a delivery wire guidable to or near an endovascular occlusion site;
   a detachable conductive coil temporarily and selectively coupled to said delivery wire; and
   an alternating current generator selectively coupled to said detachable coil for delivering damped RF power signals to said occlusion site,
   whereby a controllable occlusive apparatus efficacious and usable in small vessels is provided.

2. The apparatus of claim 1 further comprising:
   a direct current generator selectively coupled to said detachable coil; and
   a switch for selectively coupling said alternating current generator and direct current generator to said detachable coil.

3. The apparatus of claim 2 wherein said coil has a distal tip and is partially insulated at said distal tip to reduce nonuniform ohmic heating arising from direct contact of said distal tip with tissue at said occlusion site.

4. The apparatus of claim 2 wherein said direct current generator is variably controllable.

5. The apparatus of claim 2 wherein said alternating and direct current generators are variably controllable.

6. The apparatus of claim 1 wherein said coil is at least partially insulated.

7. The apparatus of claim 1 wherein said coil is selectively insulated to reduce nonuniform ohmic heating arising from direct contact between said coil and tissue at said occlusion site.

8. The apparatus of claim 1 wherein said alternating current generator is variably controllable.

9. The apparatus of claim 6 wherein said controllable alternating current generator is frequency controllable.

10. The apparatus of claim 1 further comprising a sensing circuit for determining when a predetermined state of electrocoagulation is achieved at or near said detachable coil.

11. The apparatus of claim 10 wherein said sensing circuit senses impedance of said detachable coil within said patient.

12. The apparatus of claim 10 further comprising a control circuit for selectively initiating detachment of said coil when said sensing circuit determines said predetermined state of electrocoagulation has been achieved.

13. The apparatus of claim 1 further comprising an insulator and wherein said alternating current generator serves to ohmicly heat said detachable coil and surrounding blood and tissues, but wherein local overheating is at least reduced by disposition of said insulator on at least a portion of said coil where said coil directly contacts said tissues.

14. The apparatus of claim 1 wherein said alternating current generator serves to dielectricly heat said detachable coil and surrounding blood at a radio frequency.

15. The device of claim 1 where said detachable conductive coil includes a mechanical coupling with said delivery wire and is mechanically temporarily and selectively decoupled from said delivery wire.

16. The device of claim 1 where said detachable conductive coil includes a thermally responsive coupling with said delivery wire and is temporarily and selectively decoupled from said delivery wire by use of thermal energy.

17. The device of claim 1 where said detachable conductive coil includes a optically responsive coupling with said delivery wire and is temporarily and selectively decoupled from said delivery wire by use of optical energy.

18. The device of claim 1 where said detachable conductive coil includes an electrically responsive coupling with said delivery wire and is temporarily and selectively decoupled from said delivery wire by use of electrical energy.

19. The device of claim 1 where said detachable conductive coil includes an electromagnetically responsive coupling with said delivery wire and is temporarily and selectively decoupled from said delivery wire by use of electromagnetic energy.

20. An apparatus for selectively providing endovascular occlusion in a patient comprising:
   a delivery wire guidable to or near an endovascular occlusion site;
   a detachable conductive coil temporarily and selectively coupled to said delivery wire, said coil being at least partially insulated to at least reduce local ohmic heating at points of contact between said coil and surrounding tissue at said occlusion site; and
   an alternating current generator selectively coupled to said detachable coil for delivering RF power signals to said occlusion site, wherein said alternating current generator is a radio frequency generator which generates damped radio frequency power signals,
   whereby a controllable occlusive apparatus efficacious and usable in small vessels is provided.

21. The apparatus of claim 20 further comprising a control circuit for determining when a predetermined degree of electrocoagulation has occurred at said coil and then for detaching said coil from said delivery wire.

22. An apparatus for selectively providing endovascular occlusion in a patient comprising:
   a delivery wire guidable to or near an endovascular occlusion site;
   a detachable conductive coil temporarily and selectively coupled to said delivery wire, said coil being at least partially insulated to at least reduce local ohmic heating at points of contact between said coil and surrounding tissue at said occlusion site; and
   an alternating current generator selectively coupled to said detachable coil for delivering RF power signals to said occlusion site,
   a direct current signal source electrically coupled to said detachable coil and wherein said control circuit turns said alternating current generator off when said predetermined degree of electrocoagulation has occurred and turns said direct current signal source on to detach said coil from said delivery wire,
   whereby a controllable occlusive apparatus efficacious and usable in small vessels is provided.

23. A method of forming a vascular occlusion comprising:

providing a conductive delivery wire;

disposing a conductive coil coupled to said delivery wire at or near a selected occlusion site;

applying an alternating current to said coil to coagulate said occlusion site without substantial local ohmic heating between contact points between said coil and said occlusion site;

determining whether a predetermined amount of electrocoagulation has occurred at said occlusion site;

terminating said alternating current through said coil when said predetermined amount of electrocoagulation has occurred; and detaching said coil from said delivery wire to leave said coil at said occlusion site, whereby an occlusion is efficaciously provided in a small vessel.

24. The method of claim 23 where said coil is at least partially insulated to define insulated and noninsulated portions of said coil so that application of said alternating current to said coil is through only said noninsulated portions of said coil, said insulated portions selected to include at least one of said contact points.

25. A method of forming a vascular occlusion comprising:

providing a conductive delivery wire;

disposing a conductive coil coupled to said delivery wire at or near a selected occlusion site;

applying a damped alternating current to said coil to coagulate said occlusion site;

determining whether a predetermined amount of electrocoagulation has occurred at said occlusion site;

terminating said alternating current through said coil when said step of determining establishes that said predetermined electrocoagulation has occurred; and detaching said coil from said delivery wire to leave said coil at said occlusion site, whereby an occlusion is efficaciously provided in a small vessel.

26. The method of claim 25 where said damped alternating current is applied to said coil to coagulate said occlusion site in a manner to reduce ohmic heating damage to said occlusion site.

* * * * *